United States Patent [19]

Tsuchiya

[11] Patent Number: 4,611,920
[45] Date of Patent: Sep. 16, 1986

[54] DEVICE FOR MEASURING EXTREMELY DIMINISHED INTENSITY OF LIGHT

[75] Inventor: Yutaka Tsuchiya, Hamamatsu, Japan

[73] Assignee: Hamamatsu Photonics Kabushiki Kaisha, Shizuoka, Japan

[21] Appl. No.: 532,055

[22] Filed: Sep. 14, 1983

[30] Foreign Application Priority Data

Sep. 28, 1982 [JP] Japan ............................ 57-169381

[51] Int. Cl.⁴ .......................................... G01N 21/64
[52] U.S. Cl. ..................................... 356/318; 358/93;
358/211; 250/213 VT
[58] Field of Search ............................. 356/317, 318;
250/213 VT; 313/105 CM; 358/93, 209, 211, 217

[56] References Cited

U.S. PATENT DOCUMENTS

| | | | |
|---|---|---|---|
| 3,838,996 | 10/1974 | Polaert et al. | 313/105 CM |
| 3,864,595 | 2/1975 | Lawrence et al. | 250/213 VT |
| 3,973,117 | 8/1976 | Bradley | 328/255 |
| 4,025,813 | 5/1977 | Eschard et al. | 313/105 CM |
| 4,232,333 | 12/1980 | Hiruma et al. | 358/93 |
| 4,327,285 | 4/1982 | Bradley | 250/213 VT |
| 4,352,127 | 9/1982 | Tsuchiya | 250/213 VT |
| 4,413,178 | 12/1983 | Mourou et al. | 250/213 VT |
| 4,433,236 | 2/1984 | Shimada | 250/213 VT |
| 4,434,399 | 2/1984 | Mourou et al. | 324/96 |
| 4,435,727 | 3/1984 | Schiller et al. | 358/93 |
| 4,461,572 | 7/1984 | Tsuchiya | 356/318 |

FOREIGN PATENT DOCUMENTS

| | | | |
|---|---|---|---|
| 0004729 | 10/1979 | European Pat. Off. | |
| 0151222 | 10/1981 | German Democratic Rep. | 356/318 |
| 1352732 | 5/1974 | United Kingdom | 313/105 CM |
| 2105035 | 3/1983 | United Kingdom | |

Primary Examiner—F. L. Evans
Assistant Examiner—Joel L. Harringa
Attorney, Agent, or Firm—Spencer & Frank

[57] ABSTRACT

A device for measuring an extremely diminished intensity of light by superposing a plurality of streaking images of the light beams caused by fluorescence occurring in a phosphor layer where secondary electrons are incident thereon in single photon units. A streaking image is formed by secondary electrons generated within a streaking tube through which electrons generated in a photoelectric layer therein are accelerated to the phosphor layer therein when passing through a micro-channel-plate therein. The superposed streaking images with enhanced brightness are then picked up by a television camera.

2 Claims, 5 Drawing Figures

4,611,920

DEVICE FOR MEASURING EXTREMELY DIMINISHED INTENSITY OF LIGHT

BACKGROUND

Scope of the Invention

This invention relates to a device for measuring with high sensitivity a diminished intensity of light pulses from such light emitters as organisms or organic compounds which are repeatedly being stimulated at high speed.

An important need exists for specifying the composition of an organic compound by precisely measuring a diminished intensity of light caused by fluorescence, or to locate focuses of an organism by precisely measuring a diminished intensity of light caused by fluorescence.

If the object, i.e., an organism or an organic compound is strongly stimulated, the nature of the object may change. Thus, an amount of stimulus sufficient to emit a measurable quantity of light cannot be obtained during fluorescence in many cases. It is well known that a streaking tube with a built-in micro-channel-plate can be used to measure a diminished intensity of light clocked at high speed.

Said streaking tube generates photoelectrons on its photoelectric layer responding to a diminished intensity of light. Its deflection electrode is used to deflect the electron beam of said photoelectrons, and its micro-channel-plate multiplies said photoelectrons so as to stimulate the phosphor layer located at the output of said micro-channel-plate. An intensity of multiplied light incident on the phosphor layer can thus be measured.

Sufficient brightness, in many cases, cannot be obtained on the phosphor layer even if such a device is used.

The inventors of the present invention tried to increase brightness by superposing a number of streaking images of light due to fluorescence on the phosphor layer when stimulus to the object being measured was synchronized with deflection of the streaking tube. This experiment, however, was unsuccessful.

The reason for the unsuccessful experiment was that the angle of collision of primary electrons with the dynode wall and the number of times the primary electrons collide with the dynode wall in the space between the channel inlet and outlet can vary.

The angle of collision of the primary electrons with the dynode wall affects the number of secondary electrons emitted, and the secondary electron multiplication factor increases as the angle of collision increases. The number of times the primary electrons collide affects the electron multiplication factor, and it is proportional to a certain power of the secondary electron multiplication factor defined as the frequency at which collisions occur.

The number of electrons issued from an arbitrary channel of the micro-channel-plate when a single electron is incident on that channel is distributed over a wide range of frequencies as shown at A in FIG. 1.

FIG. 1 shows that the frequency of occurrence of a fewer number of electrons emitted by collision of a single photon is higher than that of a larger number of electrons. It is well understood that the probability of occurrence of secondary electrons emitted by collision of a single photon decreases with the number of electrons.

If the streaking images obtained by a train of repetitive light pulses are superposed on the phosphor layer of said streaking tube consisting of a micro-channel-plate, a large variation can occur in the brightness of the streaking image caused by each light pulse on the phosphor layer, and a variation can also occur in the brightness of the superposed streaking images caused by repetitive light pulses. Unsatisfactory images can thus be obtained.

The quantum noise for N electrons is generally given by $N^{\frac{1}{2}}$, and thus the S/N ratio is given by $N^{\frac{1}{2}}$. One may think that the S/N ratio can be improved by the above superposition process; however, improvement is not obtained because noise is also generated by a variation in the multiplication factor of the micro-channel-plate mentioned above and the S/N ratio becomes greater than $N^{\frac{1}{2}}$. Thus, the expected result could not be obtained by the above experiment.

OBJECTIVE OF THE PRESENT INVENTION

An object of the present invention is to provide a device for measuring a diminished intensity of light in accordance with such means wherein the streaking images obtained with a micro-channel-plate, which can be used to reduce variations in the number of electrons therefrom, are superposed on the phosphor layer when a single photoelectron is incident on said micro-channel-plate, and that brightness on the phosphor layer is picked up by means of photoelectric conversion.

SUMMARY OF THE INVENTION

The device for measuring a diminished intensity of light in accordance with the present invention consists of a stimulus signal source which stimulates the object being measured so as to repetitively emit light pulses at certain intervals; a streaking tube consisting of a photoelectric layer to convert said repetitive light pulses to the corresponding electric signals, a deflection electrode to generate a deflection electric field for use in the deflection of a photoelectron, a micro-channel-plate to multiply said single photoelectron so as to generate a certain number of electrons, and a phosphor layer stimulated by electrons at the output of said micro-channel-plate; a deflection circuit for applying a sweeping voltage synchronizing with the stimulating signal from said stimulus signal source to said deflection electrodes; and detecting means for sensing brightness on the phosphor layer of said streaking tube by means of photoelectric conversion.

DETAILED DESCRIPTION OF THE PREFERRED EMBODIMENTS

Figure 2:
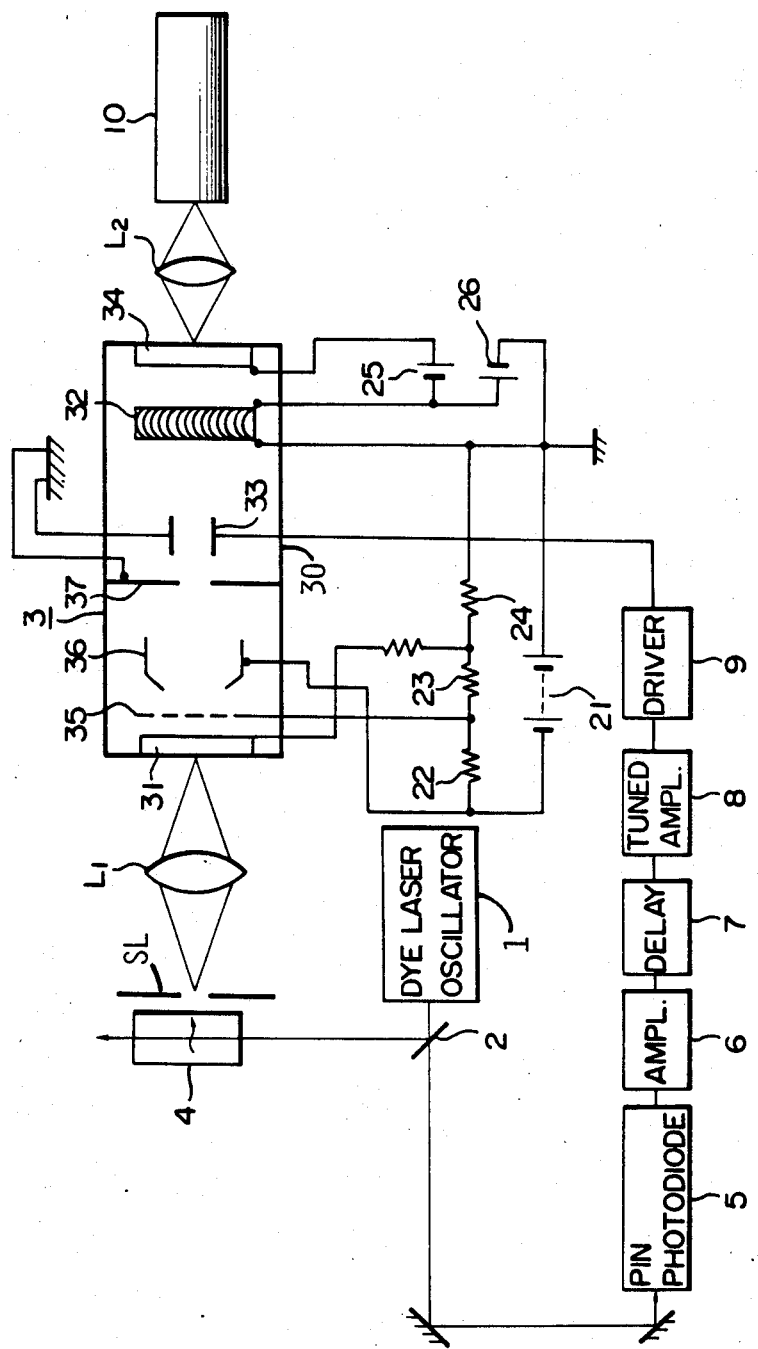
FIG. 2 shows a block diagram of an embodiment of the measuring device according to the present invention.

An embodiment of a device according to the present invention will be described hereinafter in detail referring to the drawings. FIG. 2 shows the block diagram of an embodiment of the measuring device in accordance with the present invention.

The measuring device of FIG. 2 is used to observe a diminished intensity of light caused by fluorescence from a hematoporphyrin derivative, which is an organic molecular crystal used to diagnose and treat cancer, and to specify the type of hematoporphyrin derivative.

Dye laser oscillator 1 can emit a train of 600-nm laser beam pulses with a pulse width of five picoseconds at a frequency in the range of 80 to 200 MHz.

Dye laser oscillator 1 constitutes a stimulus signal source which can repetitively issue, at said intervals, the stimulating signal to the object being measured on the measuring device of the embodiment so that the corresponding light pulses caused by fluorescence can be generated.

Semi-transparent mirror 2 constituting a beam splitter causes the light pulses from the dye laser oscillator 1 to branch into two different paths. A branching pulse laser beam is incident on a hematoporphyrin derivative 4 being measured. Fluorescence thus occurs in hematoporphyrin derivative 4 due to the stimulus by the pulse laser beam.

Light caused by fluorescence falls on photoelectric layer 31 of streaking tube 3. The number of electrons emitted from photoelectric layer 31 statistically corresponds to several tens of percents of the number of photons caused by the light beam impinging thereon.

An optical image formed in accordance with light incident on photoelectric layer 31 has an extremely narrow width in the sweeping direction of streaking tube 3. An optical projection system consisting of a slit SL lenses L1 is used for this purpose.

The other branching pulse laser beam is incident on PIN photodiode 5.

PIN photodiode 5 is a high-speed photoelectric converter with a very fast response time, and it can generate a pulse current in response to the pulse laser beam incident thereon. The output of PIN photodiode 5 is sent to tuned amplifier 8 through amplifier 6 and variable delay circuit 7.

Variable delay circuit 7 provides an appropriate delay time so as to apply the sweeping voltage to a pair of deflection electrodes 33 while photoelectrons from photoelectric layer 31 are passing through the pair of deflection electrode 33.

Tuned amplifier 8 can be operated at a frequency in the range from 80 to 200 MHz. The center frequency within the bandwidth is selected equal to the oscillation frequency of the dye laser oscillator 1.

Tuned amplifier 8 sends a sinusoidal wave signal whose frequency and phase are synchronized with the output pulse of PIN photodiode 5. The sinusoidal wave signal which is an output of tuned amplifier 8 is fed to driver 9 and then applied to deflection electrodes 33 of streaking tube 3. A sinusoidal wave amplitude applied to said deflection electrodes 33 swings from $-575$ to $+575$ volts (1150 $V_{p-p}$), and a voltage ranging from $-100$ volts to $+100$ volts is used for sweeping.

Photoelectric layer 31 is formed on the inner wall of the incident plane of envelope 30 of streaking tube 3. Phosphor layer 34 is formed opposite layer 31 on the inner wall of the incident plane. Mesh electrode 35, focusing electrode 36, aperture electrode 37, deflection electrodes 33, and micro-channel-plate 32 with concaved channels are arranged in the space between photoelectric layer 31 and phosphor layer 34.

Curved micro-channel-plate 32 is built in a frame having an outer diameter of 32.7 mm and an inner diameter of 27 mm. The frame contains parallel channels which act as secondary electron multipliers. Each channel has an inner diameter of 5 $\mu$m, and channels are arranged in 32 $\mu$m spans.

The length for each channel is selected to be 80 times the inner diameter. The axis of each channel acting as a secondary electron multiplier is at the inlet deflected 15 degrees from the main axis of curved micro-channel-plate 32. In the middle of the channel, the axis of the channel runs in parallel with the main axis. The axis of the channel is at the outlet deflected 15 degrees in the opposite direction from the main axis.

Figure 1:
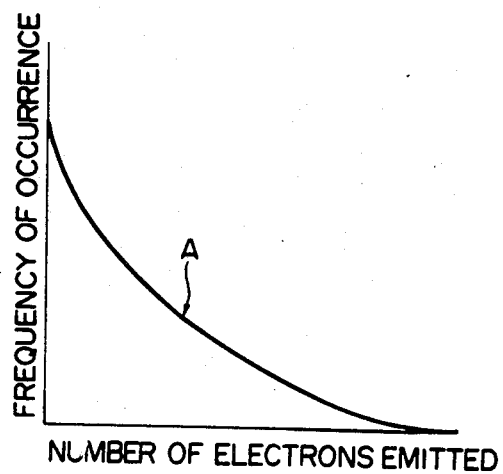
FIG. 1 is a graph showing an example of the multiplication factor of a single electron incident on the micro-channel-plate in the conventional technique.
Figure 3:
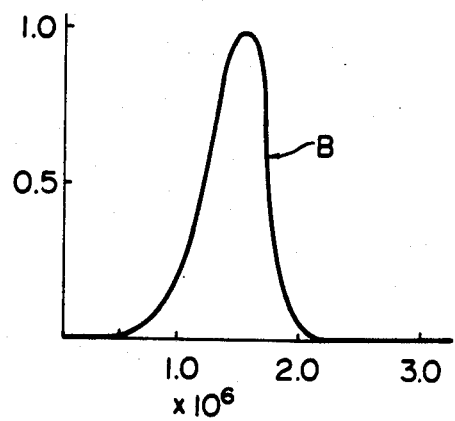
FIG. 3 is a graph showing an example of the multiplication factor of a single photoelectron incident on the micro-channel-plate used in an embodiment of the device according to the present invention.

The input electrode of the curved micro-channel-plate 32 is grounded, and its output electrode is kept at 1500 volts DC. As shown by curve B of FIG. 3, when an electron strikes the input electrode, electrons with a distribution having a narrow half-value width of $6 \times 10^5$ centered at $1.5 \times 10^6$ are emitted from the output electrode. Both the input electrode of micro-channel-plate 32 and aperture electrode 37 are grounded. Photoelectric layer 31 is kept at $-4000$ volts DC, the mesh electrode at $-3000$ volts DC, and the focusing electrode at $-3100$ volts DC. These voltages are determined by both power supply 21 and a voltage divider consisting of resistors 22 through 24. Phosphor layer 34 is kept at as high a voltage as 3000 volts DC by power supply 25 with respect to the output electrode of curved micro-channel-plate 32. The output electrode of curved micro-channel-plate 32 is kept at 1500 volts DC by power supply 26.

Television camera 10 is installed to pick up images on the phosphor layer of streaking tube 3. The horizontal trace of television camera 10 is kept at right angles with respect to the trace of streaking tube 3.

Figure 4:
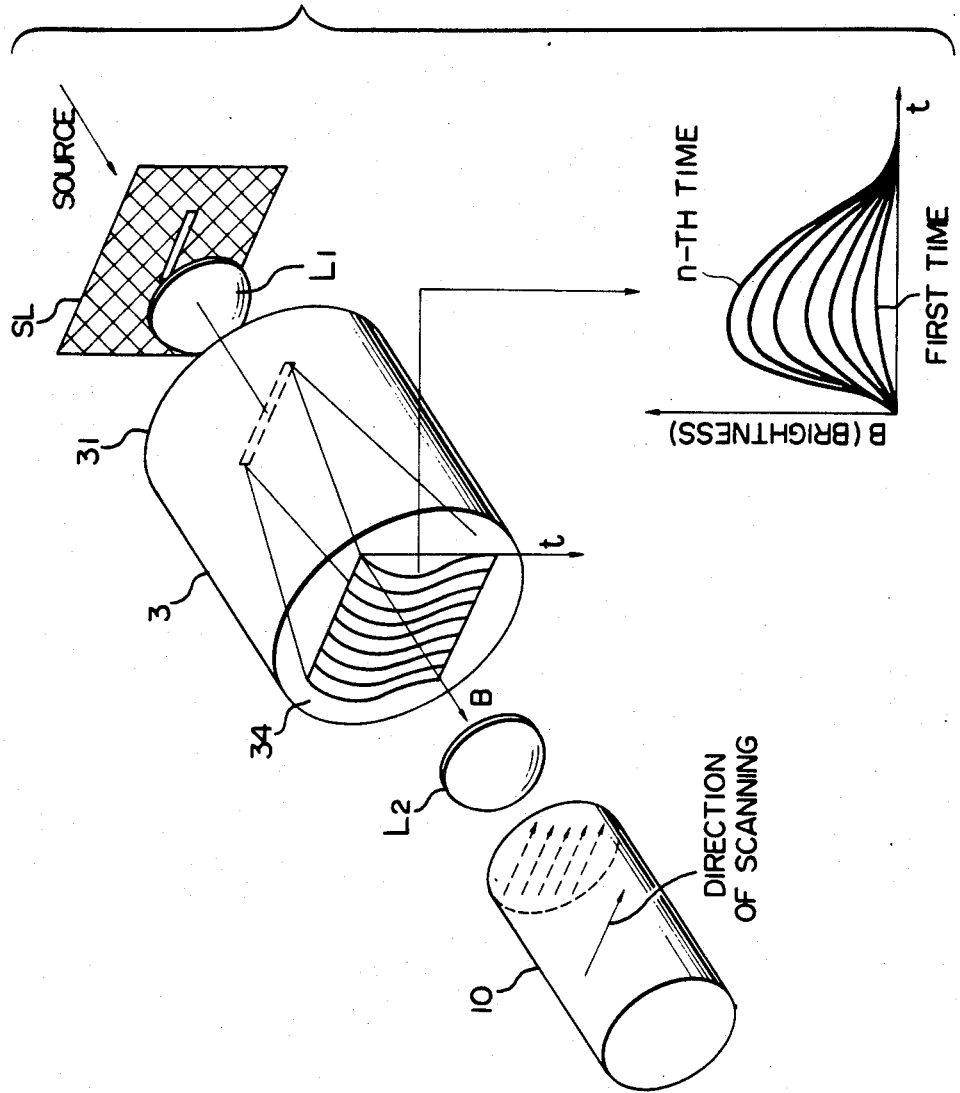
FIG. 4 is an illustration depicting the operation of the device in accordance with the present invention.

Operation of said camera device will be described referring to FIG. 4. FIG. 4 shows the principle of operation of said camera device.

Light caused by fluorescence occurring in hematoporphyrin derivative 4, recognized as an organic molecular crystal which can emit light pulses during stimulation by means of the output pulse laser beam of dye laser oscillator 1 used as a stimulus signal source, is incident upon photoelectric layer 31 of said streaking tube 3 after passing through slit SL and lens L1.

An image consisting of a plurality of lines as shown in FIG. 4 is formed by fluorescence on photoelectric layer 31 of streaking tube 3.

Photoelectrons generated within photoelectric layer 31 of said streaking tube 3 are accelerated and go into phosphor layer 34, passing through the streaking tube. During acceleration, these electrons are deflected by sweeping voltages applied across said deflection electrodes 33 (see FIG. 2). Deflection is orthogonal to said streaking image formed by fluorescence.

The retracing sweeping voltages can be generated in the reverse direction when sweeping is carried out to form the streaking image. In this case, no photoelectrons can exist within the electric deflection field and thus the streaking image in the reverse direction cannot be overlapped.

The sweeping voltage applied to deflection electrode 33 is synchronized with the output laser pulse beams of dye laser oscillator 1 used as a stimulus signal source thereby causing fluorescence to occur.

The streaking images of light beams caused by said fluorescence are repeatedly superposed on a certain portion of phosphor layer 34, and the superposed streaking images can be displayed on the streaking tube. Both coordinates of the time and brightness for different streaking images are also overlapped on phosphor layer 34.

If the streaking images of light beams caused by fluorescence due to stimulus by means of a dye laser operating at a repetition rate of 100 MHz are superposed for a time of one second so as to form a combined image, the streaking images count $10^8$. Even if a photon is generated when $10^3$ to $10^4$ stimuli are applied to the object, measurement of an extremely diminished intensity of light can thus be obtained.

The superposed streaking images with higher brightness can be picked up by television camera 10. The horizontal trace of television camera 10 runs orthogonal to said time coordinate, and brightness information can be displayed along the horizontal line defining the time. Information indicating a change with time in the intensity of light caused by fluorescence from hematoporphyrin derivative 4 can be obtained by analyzing the above video signal. The type of hematoporphyrin derivative 4 can thus be specified by analyzing the intensity of light caused by fluorescence with respect to time.

Figure 5:
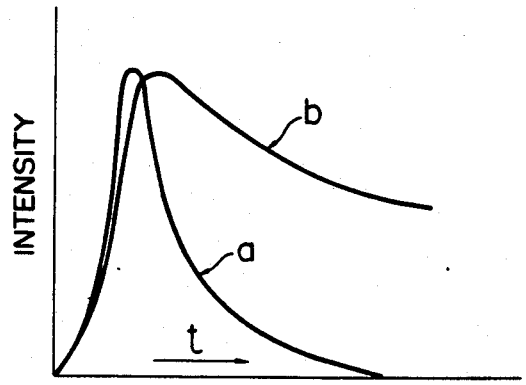
FIG. 5 is a graph of an example of fluorescence which has occurred in a hematoporphyrin derivative.

FIG. 5 shows plots of the light beams caused by fluorescence from typical hematoporphyrin derivatives as examples a and b.

The plots of the light beams caused by fluorescence represent the chemical properties and structures of the materials. A specific type of hematoporphyrin derivative used to treat cancer can thus be specified utilizing the plots and the chemical structure of the special type of hematoporphyrin derivative can be defined. When doped into the human body, some types of hematoporphyrin derivatives are known to concentrate into the organism where cancer has occurred. This property can be utilized to detect and treat cancer.

In accordance with the present invention each photoelectron recognized as an element of the streaking image can thus be multiplied to obtain a certain number of electrons and these electrons can be displayed on the phosphor layer to form a streaking image generated by superposing these electrons. A video signal is then obtained by picking up the image on the phosphor layer. A video signal with high S/N ratio can thus be obtained from the streaking image even though an extremely diminished intensity of light is generated by fluorescence. In accordance with the present invention, it is therefore advantageous that an insensible intensity of light from the object can be changed to a detectable intensity of light by superposing electrons within a secondary electron multiplier before being picked up by the television camera.

Modifications of the embodiment of the present invention which has been described herein are possible.

Curved micro-channels are used in a micro-channel-plate in the embodiment of the present invention which has been cited.

Another embodiment uses a pair of channel plates where the biasing angles between the respective channel axes and micro-channel-plates are alternately reversed to form luminated leaves of each channel plate, a triple set of channel plates of the same structure, and a channel plate where holes of its luminated leaves are arranged in displaced positions. Furthermore, the distribution of electrons issued from the micro-channel-plates responding to a single photoelectron can be narrowed by the saturated maximum current characteristics at the output thereof.

What is claimed is:

1. A device for measuring an extremely diminished intensity of light comprising:
    a stimulus signal source which stimulates an object being measured so as to repetitively emit light pulses at predetermined timing intervals;
    a streaking tube including
        a photoelectric layer for converting said repetitive light pulses to corresponding electric signals;
        a deflection electrode for generating a deflection electric field for deflecting a single photoelectron;
        a micro-channel-plate consisting of curved microchannels for multiplying said single photoelectron so as to generate a plurality of electrons at the output thereof, the distribution of said electrons having a narrow half-value centered at a predetermined frequency of occurrence;
        a phosphor layer stimulated by electrons at the output of said micro-channel-plate, a spot having approximately the same brightness for each of said single photoelectrons being formed on the surface of said phosphor layer whereby the brightness of said spot corresponds to the number of multiplied electrons;
    a deflection circuit for applying, to said deflection electrode, a sweeping voltage synchronized with the stimulating signal issued from said stimulus signal source; and
    detecting means for detecting the brightness of said spot on the phosphor layer of said streaking tube by means of photoelectric conversion, said detecting means being a television imaging device wherein the horizontal trace thereof extends orthogonally to the direction of deflection of said streaking tube.

2. A device for measuring an extremely diminished intensity of light as claimed in claim 1, wherein said stimulus signal source is a dye laser oscillator.

* * * * *

UNITED STATES PATENT AND TRADEMARK OFFICE
CERTIFICATE OF CORRECTION

PATENT NO. : 4,611,920

DATED : September 16, 1986

INVENTOR(S) : Yutaka Tsuchiya

It is certified that error appears in the above-identified patent and that said Letters Patent is hereby corrected as shown below:

Please correct Col. 3, line 52 to read as follows:

-- deflection electrodes 33. --

Signed and Sealed this

Twelfth Day of June, 1990

Attest:

HARRY F. MANBECK, JR.

*Attesting Officer*     *Commissioner of Patents and Trademarks*